United States Patent [19]

Berstermann et al.

[11] Patent Number: 4,544,270

[45] Date of Patent: Oct. 1, 1985

[54] APPARATUS FOR THE SPECTROGRAPHIC ANALYSIS OF WORKPIECES FORMED FROM IRON AND STEEL ALLOYS

[75] Inventors: Wilhelm Berstermann; Ulrich Grisar, both of Georgsmarienhütte; Egon Koerfer, Osnabrück, all of Fed. Rep. of Germany

[73] Assignee: Klöckner-Werke Aktiengesellschaft, Duisburg, Fed. Rep. of Germany

[21] Appl. No.: 482,985

[22] Filed: Apr. 7, 1983

[30] Foreign Application Priority Data

Apr. 14, 1982 [DE] Fed. Rep. of Germany ....... 3213660

[51] Int. Cl.$^4$ .............................. G01N 21/67

[52] U.S. Cl. .............................. 356/313

[58] Field of Search .............................. 356/313, 328

[56] References Cited

U.S. PATENT DOCUMENTS 3,909,133 9/1975 Hobson et al. .............................. 356/313
4,037,963 7/1977 Grisar et al. .............................. 356/313
4,074,936 2/1978 Grisar et al. .............................. 356/313
4,111,556 9/1978 Grisar et al. .............................. 356/313
4,411,524 10/1983 Kremer et al. .............................. 356/313

FOREIGN PATENT DOCUMENTS 2513379 10/1976 Fed. Rep. of Germany .
2513267 5/1977 Fed. Rep. of Germany .
2513266 1/1978 Fed. Rep. of Germany .
2406192 6/1979 France .............................. 356/313

*Primary Examiner*—F. L. Evans
*Attorney, Agent, or Firm*—Watson, Cole, Grindle & Watson

[57] ABSTRACT

The determination, through spectrographic analysis, of the C content of iron and steel alloy workpieces via the C 1931.02 line is made using spectrometers having a test head that can be attached to the workpiece. The region of the discharge near the surface of the workpiece is isolated in an argon atmosphere from the light path of the discharge to be imaged onto the grating, so that the two unwanted iron lines, the Fe 1931.4 and the Fe 1930.8 lines, do not occur in the grating spectrum.

2 Claims, 5 Drawing Figures

3
6
7
5
2
4
8
10
11
9

APPARATUS FOR THE SPECTROGRAPHIC ANALYSIS OF WORKPIECES FORMED FROM IRON AND STEEL ALLOYS

BACKGROUND OF THE INVENTION

1. Field of the Invention

This invention relates to a method and apparatus for the spectrographic analysis of workpieces formed from iron and/or steel alloys, and more particularly to a method and apparatus wherein a test head of a spectrometer is attached to a workpiece to be analyzed whereupon a unipolar discharge is triggered between the counterelectrode of the test head and the workpiece. Light generated from the discharge is imaged onto a grating of the spectrometer.

2. Description of the Prior Art

Spectrometers have long been known in the iron and steel producing industry. As a rule, stationary laboratory instruments have been employed which have the drawback that material samples have to be separated from the workpiece to be analyzed and placed in the spectrometer in the laboratory. Efforts have also been made to determine the alloy constituents of workpieces without separating the material samples from the workpieces by using transportable spectrometers available on the market which utilize a transportable test head.

However, whereas the carbon constituent of iron or steel alloys can readily be analyzed with the stationary units noted above, it has been found that in the case of the prior art transportable units no interpretable effects have been produced. In addition to the C1931.02 carbon line occurring in the stationary units, two additional lines are found that are partly superimposed with the carbon line, so that evaluation of the carbon line is not possible. These are the Fe1931.4 and Fe1930.8 iron lines. Particularly aggravating is the fact that the intensity of these lines is not constant for the same workpiece, which results in failure of the conventional electronic devices. For a long time these effects could not be interpreted. Accordingly, the transportable spectrometer according to the invention was developed to overcome such drawbacks and to allow analysis of workpieces outside of the laboratory. The transportable spectrometer was developed in accordance with the comparative principle set forth in German Pat. Nos. 25 13 266, 25 13 267, and 25 13 279.

SUMMARY OF THE INVENTION

The spectrometer according to the invention has a test head which is attached to the workpiece to be analyzed, such as to a single bar of packaged bar stock. Between the counter-electrode in the test head and the workpiece to be analyzed there is triggered a discharge which is imaged optically onto a Rowland grating of the spectrometer through an outlet orifice or outlet window. The image may be transmitted to the spectrometer through the use of an optical fiber. The intensities of the spectral lines of the elements concerned are evaluated as in the stationary units in a manner known from the prior art.

The inventors discovered that the unwanted iron lines noted above occur only in the immediate vicinity of the spark-off area of the workpiece. Based on this knowledge, the object of the invention is to provide a method of the type referred to above wherein the carbon determination is made possible with spectrometers having a test head that can be mounted on, or attached to, the workpiece.

The problem of accurate carbon content determination is solved in accordance with the invention by using the spectral analytical determination of the carbon content by means of the C1931.02 line by isolating a region of the discharge at the surface of the material sample to be analyzed from the light path of the discharge to be imaged, such that the two unwanted iron lines do not occur in the grating spectrum. These lines are the Fe1931.4 and Fe1930.8 iron lines. It is essential that the grating not only does not "see" the sample surface in the discharge region, but that this part of the discharge is not imaged.

In principle, this process can be carried out in such a way that the imaging of the discharge takes place by means of a light path parallel to, and spaced a given distance from, the surface of the workpiece to be tested. It has been found that a distance of about 1 mm is adequate. According to the invention, an aperture is placed in the light path so that, to a certain extent, the discharge region near the workpiece surface lies in its shadow.

According to one preferred embodiment of the invention the test head is provided with a plate which comes into abutting engagement with the surface of the material sample and has a bore formed therein for passage of the discharge between the counterelectrode and the workpiece to be analyzed. The plate includes a recess which is parallel to, and spaced a distance from, the material sample and opens into the recess into which an optical fiber is inserted. The remaining thickness of the plate functions as an aperture so that the discharge region near the surface of the material sample is isolated from the light path.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein.

DETAILED DESCRIPTION OF THE PREFERRED EMBODIMENT

Figure 1A:
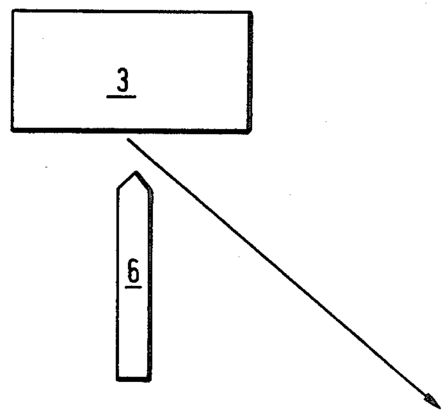
FIG. 1*a* is a schematic diagram of a prior art spectrometer arrangement.
Figure 1B:
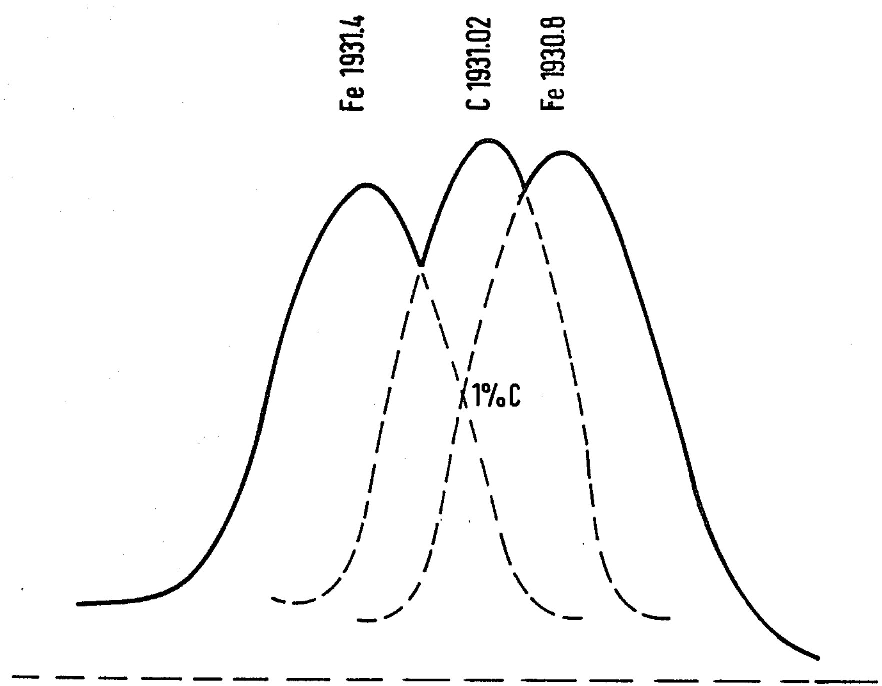
FIG. 1*b* is a portion of a grating spectrum showing the carbon line and two iron spectral lines such as measured in presently known spectrometers having an attachable test head as in FIG. 1*a;*
Figure 2A:
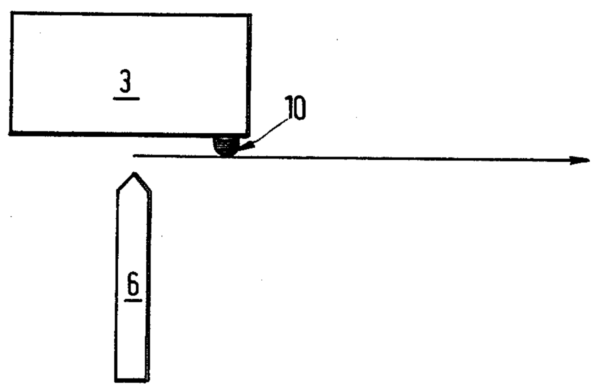
FIG. 2*a* is a schematic diagram of a spectrometer arrangement according to the present invention.
Figure 2B:
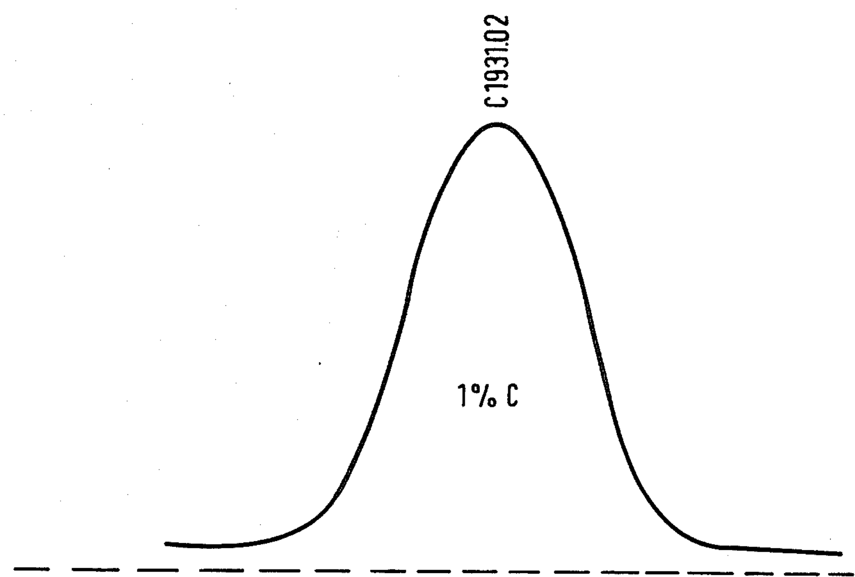
FIG. 2*b* shows a grating spectrum corresponding to the illustration in FIG. 1*b* but using the test head according to the invention.

FIG. 1*b* shows that the 1931.02 carbon spectral line is partly superimposed by two iron spectral lines when prior art transportable spectrometers are employed as shown in FIG. 1*a,* wherein light leakage from the discharge is shown to travel at an angle with respect to the surface of the workpiece 3. FIG. 2*b* shows the light spectrum with a test head according to the invention as schematically depicted in FIG. 2*a* wherein light leakage from the counterelectrode discharge is shown to travel parallel to the surface of the workpiece.

Figure 3:
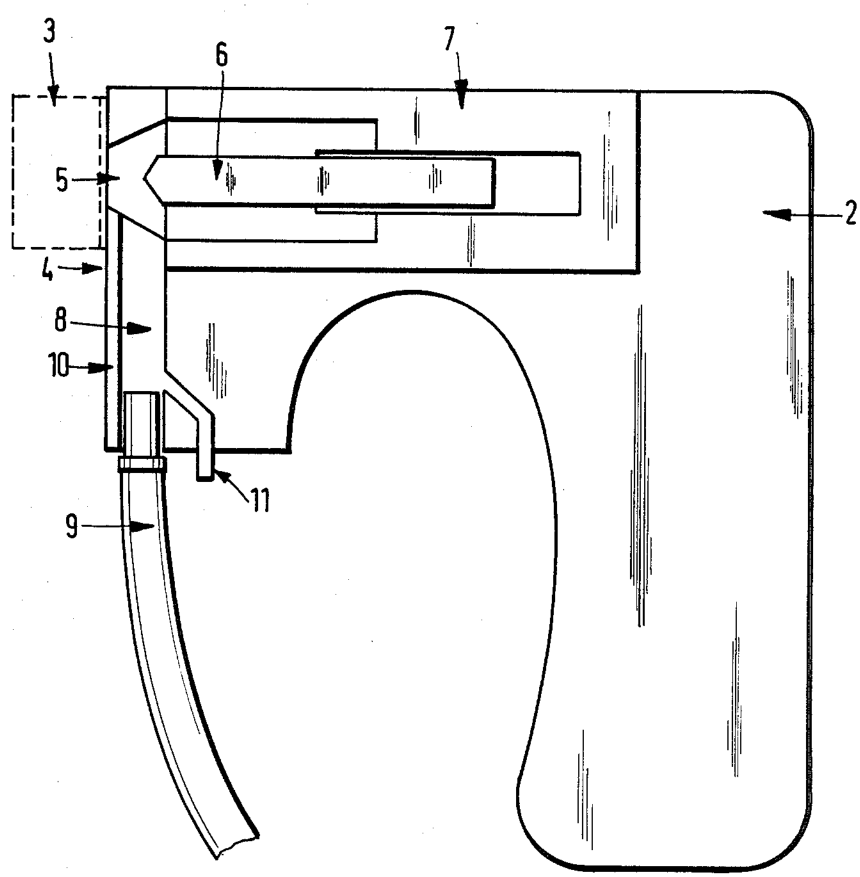
FIG. 3 depicts, in section, one embodiment of the test head according to the invention.

FIG. 3 is a schematic representation of one embodiment of the test head according to the invention in longitudinal section showing the housing 2 of the test head. The housing 2 has provided in its side facing the workpiece 3 a plate 4 having a bore 5 formed therein, above which a counterelectrode 6 is placed in an insulated socket body 7 in a manner known from the prior art.

The plate 4 has a recess or groove 8 spaced a given predetermined distance from, and parallel to, the surface of the material sample. The recess 8 opens into the bore 5 and forms a light path. An optical fiber 9 is inserted into recess 8 and leads in a manner known from the prior art to the spectrometer member (not shown) and to the grating.

The housing 2 has an inlet connection 11 for argon. The argon is fed through inlet 11 such that a region of the surface of the sample material is isolated, in an argon atmosphere, from the light path of the discharge. In this manner, the unwanted spectrographic iron lines are not imaged on the grating spectrum of the spectrograph.

Between the workpiece 3 to be analyzed and the counter-electrode 6, a unipolar discharge is triggered in a known manner. The aperture 10 isolates the region near the workpiece from the discharge. The residual radiation emitted from the discharge reaches the optical fiber 9, whereby, owing to the chosen geometry, the discharge region containing the excited iron atoms is isolated from the optical fiber.

The measures advocated by the invention remedy in a surprising manner a drawback that has existed for many years and which heretofore has ruled out the use of prior art transportable spectrometers for direct carbon analysis of the workpiece. That is, the prior art required that a material sample be separated from the workpiece and analyzed with a stationary spectrometer within a laboratory. Such drawbacks are obviated with the instant invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A portable test head which is attachable to a portable spectrometer and which can be positioned against a workpiece containing iron and steel alloys in order to accomplish a spectrographic analysis of the carbon line 1931.02, said test head comprising a housing, said housing having a front side intended to face a workpiece to be analyzed and an inlet connection which communicates with said front side;

a plate positioned on said front side of said housing, said plate having a flat external surface which is abuttable against a workpiece to be analyzed and a peripheral edge, a bore extending therethrough from said flat external surface toward said front side of said housing, and an elongated recess which extends therethrough in parallel with said flat external surface from said bore therein to its peripheral edge, said recess communicating with said inlet connection in said housing;

a single counterelectrode mounted within said housing, said single counterelectrode extending toward said bore in said plate; and a light conductor having opposite ends, one of said opposite ends extending into said recess in said plate at the periphery thereof and the other of said opposite ends being connectable to a portable spectrometer;

light resulting from a unipolar discharging passing from said counterelectrode through said bore and striking a workpiece positioned against said flat external surface of said plate passing through said recess in said plate which contains argon gas supplied through said inlet connection in said housing and into said light conductor, said light conductor being shielded by said plate from a direct viewing of said workpiece.

2. The portable test head as claimed in claim 1, including an insulating body supporting said counterelectrode within said housing.

* * * * *